United States Patent

Diaz et al.

[11] Patent Number: 5,567,836
[45] Date of Patent: Oct. 22, 1996

[54] PROCESS FOR SEPARATION OF METHYLTRICHLOROSILANE FROM DIMETHYLDICHLOROSILANE

[75] Inventors: Michael Diaz, Lexington, Ky.; Roland L. Halm; Michael A. McIntyre, both of Midland, Mich.; Oliver K. Wilding, Lagrange, Ky.

[73] Assignee: Dow Corning Corporation, Midland, Mich.

[21] Appl. No.: 564,550

[22] Filed: Nov. 29, 1995

[51] Int. Cl.⁶ .................................................. C07F 7/08
[52] U.S. Cl. .............................. 556/466; 210/694
[58] Field of Search ................. 556/466; 210/694

[56] References Cited

U.S. PATENT DOCUMENTS

| | | | |
|---|---|---|---|
| 3,168,542 | 2/1965 | Shaffer | 556/466 |
| 3,441,584 | 4/1969 | Bazouin et al. | 556/466 |
| 3,646,092 | 2/1972 | Dathe | 556/466 |
| 4,402,796 | 9/1983 | Marko et al. | 556/466 X |
| 4,411,740 | 10/1983 | Flannigam et al. | 556/466 X |
| 5,290,342 | 3/1994 | Wikman et al. | 95/143 |
| 5,445,742 | 8/1995 | Almquist et al. | 210/670 |

*Primary Examiner*—Paul F. Shaver
*Attorney, Agent, or Firm*—William F. Boley

[57] ABSTRACT

A process for separating methyltrichlorosilane from dimethyldichlorosilane in a mixture. The process comprises contacting a mixture comprising methyltrichlorosilane and dimethyldichlorosilane with activated carbon, where the methyltrichlorosilane is selectively adsorbed by the activated carbon. The process allows for the recovery of a dimethyldichlorosilane fraction reduced in methyltrichlorosilane concentration. The methyltrichlorosilane can be recovered by desorption from the activated carbon. The present process is especially useful for removing low levels of methyltrichlorosilane present as a contaminate in dimethyldichlorosilane.

9 Claims, No Drawings

5,567,836

PROCESS FOR SEPARATION OF METHYLTRICHLOROSILANE FROM DIMETHYLDICHLOROSILANE

BACKGROUND OF INVENTION

The present invention is a process for separating methyltrichlorosilane from dimethyldichlorosilane in a mixture. The process comprises contacting a mixture comprising methyltrichlorosilane and dimethyldichlorosilane with activated carbon, where the methyltrichlorosilane is selectively adsorbed by the activated carbon. The process allows for the recovery of a dimethyldichlorosilane fraction reduced in methyltrichlorosilane concentration. The methyltrichlorosilane can be recovered by desorption from the activated carbon. The present process is especially useful for removing low levels of methyltrichlorosilane from dimethyldichlorosilane.

The commercial production of methylchlorosilanes involves the contact of methyl chloride with silicon metalloid in the presence of a catalyst comprising copper at temperatures within a range of about 300° C. to 350° C. Typically this process is optimized for the production of dimethyldichlorosilane, with lessor amounts of methylsilanes, methylchlorosilanes, methylhydrosilanes, $C_2$ to $C_7$ hydrocarbons, polysilanes, polysiloxanes, silylmethylenes, and other species being formed. This product mixture usually undergoes a series of process steps such as distillation, condensation, and the like to effect separation and recovery of commercially important individual components of the product mixture. However, standard separation techniques based on the difference in the boiling point between compounds become difficult and expensive when the compounds have similar boiling points. This situation exists with the separation of methyltrichlorosilane (b.p. 66.1° C.) and dimethyldichlorosilane (b.p. 70.1° C.). The present inventors have found that activated carbon selectively adsorbs methyltrichlorosilane when in mixture with dimethyldichlorosilane and therefore provides an alternative method for separation of these two methylchlorosilanes. The present process has been found particularly effective for removing trace amounts of methyltrichlorosilane from dimethyldichlorosilane, thereby providing dimethyldichlorosilane essentially free of methyltrichlorosilane contamination.

Wilkman et al., U.S. Pat. No. 5,290,342, describe a process for separating ethylsilane from silane by selective adsorption of the ethylsilane onto activated carbon.

Bothe et al., U.S. Pat. No. 5,445,742, describe a process for purification of halosilanes. The process consists of contacting a mixture comprising a halosilane and a hydrocarbon with an adsorbent selective for the hydrocarbon. Examples of useful adsorbents taught by Bothe et al. include activated carbon, carbon molecular sieves, and high silica zeolite.

The cited art does not recognize that activated carbon can be used as a selective adsorbent to separate methyltrichlorosilane from dimethyldichlorosilane.

SUMMARY OF INVENTION

The present invention is a process for separating methyltrichlorosilane from dimethyldichlorosilane in a mixture. The process comprises contacting a mixture comprising methyltrichlorosilane and dimethyldichlorosilane with activated carbon, where the methyltrichlorosilane is selectively adsorbed by the activated carbon. The process allows for the recovery of a dimethyldichlorosilane fraction reduced in methyltrichlorosilane concentration. The methyltrichlorosilane can be recovered by desorption from the activated carbon. The present process is especially useful for removing low levels of methyltrichlorosilane present as a contaminate in dimethyldichlorosilane.

DESCRIPTION OF INVENTION

The present invention is a process for separating methyltrichlorosilane from dimethyldichlorosilane in a mixture. The process comprises (A) contacting a mixture comprising methyltrichlorosilane and dimethyldichlorosilane with activated carbon, where the methyltrichlorosilane is selectively adsorbed by the activated carbon and (B) recovering dimethyldichlorosilane reduced in methyltrichlorosilane concentration. The process can further comprise (C) recovering the adsorbed methyltrichlorosilane by desorption from the activated carbon.

In a preferred process the dimethyldichlorosilane is present as a major component of the mixture while the methyltrichlorosilane is present as a minor component of the mixture. More preferred is when the methyltrichlorosilane comprises less than about 10 weight percent of the mixture. The mixture may comprise as minor components other compounds including methylchlorosilanes and similar boiling hydrocarbons.

The mixture comprising the methyltrichlorosilane and dimethyldichlorosilane can be contacted with the activated carbon by standard methods. The process can be run as a batch process, semi-continuous, or continuous process. The mixture comprising the methyltrichlorosilane and dimethyldichlorosilane can be contacted in the liquid or gas phase with the activated carbon. Preferred is when the mixture is in the liquid phase when contacted with the activated carbon.

The temperature at which the mixture comprising the methyltrichlorosilane and dimethyldichlorosilane is contacted with the activated carbon is not critical and can generally be within a range of about 0° C. to less than 180° C. A preferred temperature is within a range of about 10° C. to 50° C. The pressure at which the mixture comprising methyltrichlorosilane and dimethyldichlorosilane is contacted with the activated carbon is not critical and can generally be within a range of about 0.1 atm. to 10 atm. Preferred is when the process is conducted at a pressure of about 1 atm. to 5 atm.

In a preferred process the mixture is contacted with one or more packed-beds of the activated carbon operated in a temperature swing adsorption (TSA) mode. For example, the mixture can be passed through a first packed-bed of activated carbon until the activated carbon is nearly saturated with methyltrichlorosilane, the mixture can then be diverted to second packed-bed of activated carbon. The methyltrichlorosilane can then be recovered from the nearly saturated bed of activated carbon by heating the bed to a temperature causing desorption of the methyltrichlorosilane from the activated carbon. A heated inert sweep gas such as nitrogen may be passed through the saturated bed to facilitate desorption and recovery of the methyltrichlorosilane. Typically, desorption of the methyltrichlorosilane can be effected at a temperature above about 60° C. Preferred is when the desorption temperature is within a range of about 100° C. to 400° C. The mixture can then be switched between the activated carbon beds allowing for the activated carbon beds to be alternated between an adsorption and desorption mode, thereby providing for a continuous process.

The physical form of the activated carbon is not critical to the present invention and can be, for example, flakes, chips, pellets, and powder. By "activated carbon" it is meant a microcrystalline, nongraphite form of carbon, having an internal porosity, the carbon having been activated by standard methods known in the art for producing activated carbon. For Example, the activated carbon can be formed by chemical or gas activation processes as described in Kirk-Othmer, Concise Encyclopedia of Chemical Technology, John Wiley & Sons, New York, p. 204–205, 1985. The activated carbon can be, for example, bituminous coal-based coconut shell-based, wood-based, or peat-based.

Since chlorosilanes rapidly hydrolyze upon contact with water to form gels, it may be desirable to dry the activated carbon prior to use in the present process. The activated carbon can be dried by standard techniques such as heating or heating along with reduced pressure to reduce residual water. An example of useful conditions for drying the activated carbon is described in the Examples herein.

The activated carbon selectively adsorbs methyltrichlorosilane relative to dimethyldichlorosilane in a mixture. This selectivity allows for recovery of dimethyldichlorosilane reduced in methyltrichlorosilane concentration. Recovery of the dimethyldichlorosilane reduced in methyltrichlorosilane can be effected by standard methods for separating gases or liquids from solids. In the preferred process using a packed-bed of activated carbon, recovery of the dimethyldichlorosilane can consist of collecting the effluent from the column in a suitable container for chlorosilanes.

The present process can further comprise recovery of the methyltrichlorosilane by desorption from the activated carbon. Desorption of the activated carbon can be effected by standard means such as using elevated temperatures, reduced pressure, or a combination of both as described above for the preferred continuous process.

The following examples are provided to illustrate the present invention. These examples are not intended to limit the scope of the claims herein.

EXAMPLE

Several activated carbons were evaluated for their ability to selective adsorb methyltrichlorosilane from a mixture consisting of dimethyldichlorosilane containing either about 1500 ppm or about 2100 ppm methyltrichlorosilane. Each activated carbon sample was placed in a 50 ml flask. The carbon sample size ranged between 10 to 20 grams. The flask was heated at about 350° C. under vacuum at about 30 mm Hg for six to eight hours to dry the activated carbon. The flask was cooled and purged with dry nitrogen. The chlorosilane mixture was then injected into the cooled flask through a Viton rubber septum. An additional seal was provided by a teflon stop-cock. The flask was shaken at room temperature for about 16 hours. A liquid sample was taken from the flask and analyzed by gas chromatography using a flame ionization detector (GC-FID). The result of this analysis is reported in Table 1 under the heading "1st Pass". The activated carbon was then regenerated by heating at 350° C. under vacuum at about 30 mm Hg for six to eight hours. The flask was cooled, purged with dry nitrogen, and a second aliquot of the chlorosilane mixture injected into the flask. After shaking the flask for about 16 hours at room temperature a liquid sample was taken from the flask and analyzed by GC-FID. The results of this analysis are reported in Table 1 under the heading "2nd Pass". The activated carbons tested were products of either Calgon, Pittsburgh, Pa.; or Norit America Atlanta, Ga. as indicated in Table 1. The manufacturer's designation for each of the activated carbons is also provided in Table 1 along with the identity of the carbonaceous base material from which the activated carbon was formed.

Because of the variability in adsorbent to liquid ratios used in the testing of the activated carbons the results of the adsorption tests are reported in Table 1 as the effective Henry's Law coefficient. The effective Henry's Law coefficient is calculated as $H=X_c/Y_c$, where $X_c$ is the adsorbent's equilibrium loading of methyltrichlorosilane (i.e. mass of methyltrichlorosilane adsorbed per unit mass of adsorbent) and $Y_c$ is the methyltrichlorosilane liquid equilibrium concentration (mass/mass). All activated carbons described in Table 1 were effective in selectively adsorbing methyltrichlorosilane. The larger the Henry's Law coefficient the higher the adsorption capacity of the activated carbon for the methyltrichlorosilane.

TABLE 1

Activated Carbon Selectivity For Methyltrichlorosilane Adsorption

| Manufacturer | Designation | Henry's Coefficient | |
| --- | --- | --- | --- |
| | | 1st Pass | 2nd Pass |
| Calgon | (a)PCB-G Pulv | 4.4 | 1.6 |
| Norit | (b)Norit C | 3.7 | 1.9[a] |
| Calgon | (c)CPG 12 X 40 | 2.7 | 0.7 |
| Calgon | (b)114A-AWD | 2.6 | 1.2 |
| Norit | (c)GCW 12 X 40 | 2.3 | 1.1[a] |
| Calgon | (c)XtruSorb 600 | 2.0 | 0.7 |
| Calgon | (c)APA 12 X 40 | 2.0 | 1.0 |
| Calgon | (c)XtruSorb 700 | 1.9 | 0.7 |
| Norit | (d)PK 1-3 | 1.0[a] | — |
| Calgon | (c)CAL 12 X 40 | 0.6 | 0.3 |

Base material = (a)coconut shell, (b)wood, (c)bituminous coal, (d)peat.
[a]Initial concentration of methyltrichlorosilane about 2,100 ppm

We claim:

1. A process for separation of methyltrichlorosilane from dimethyldichlorosilane, the process comprising:

(A) contacting a mixture comprising methyltrichlorosilane and dimethyldichlorosilane with activated carbon, where the methyltrichlorosilane is selectively adsorbed by the activated carbon and (B) recovering dimethyldichlorosilane reduced in methyltrichlorosilane concentration.

2. A process according to claim 1, further comprising (C) recovering the adsorbed methyltrichlorosilane by desorption from the activated carbon.

3. A process according to claim 1, where the dimethyldichlorosilane is present in the mixture as a major component and the methyltrichlorosilane is present in the mixture as a minor component.

4. A process according to claim 1, where the methyltrichlorosilane comprises less than about 10 weight percent of the mixture.

5. A process according to claim 1, where the mixture is in the liquid phase when contacted with the activated carbon.

6. A process according to claim 1, where the mixture is contacted with the activated carbon at a temperature within a range of about 10° C. to 50° C.

7. A process according to claim 1, where the mixture is contacted with one or more packed-beds of the activated carbon operated in a temperature swing adsorption mode.

8. A process according to claim 2, where desorption of the methyltrichlorosilane from the activated carbon is effected at a temperature within a range of about 100° C. to 400° C.

9. A process for separation of methyltrichlorosilane from dimethyldichlorosilane, the process comprising:

(A) contacting a liquid mixture comprising methyltrichlorosilane as a minor component and dimethyldichlorosilane as a major component with activated carbon at a temperature within a range of about 10° C. to 50° C., where the methyltrichlorosilane is selectively adsorbed by the activated carbon, (B) recovering dimethyldichlorosilane reduced in methyltrichlorosilane, and (C) recovering the adsorbed methyltrichlorosilane by desorption from the activated carbon.

* * * * *